United States Patent [19]

Davis

[11] Patent Number: 4,968,827
[45] Date of Patent: Nov. 6, 1990

[54] ALKYLALUMINOXANE PROCESS

[75] Inventor: Robert L. Davis, Baton Rouge, La.

[73] Assignee: Ethyl Corporation, Richmond, Va.

[21] Appl. No.: 362,085

[22] Filed: Jun. 6, 1989

[51] Int. Cl.$^5$ ............................................... C07F 5/06
[52] U.S. Cl. ..................................... 556/179; 556/175
[58] Field of Search ................................. 556/179, 175

[56] References Cited

U.S. PATENT DOCUMENTS

| | | | |
|---|---|---|---|
| 3,242,099 | 3/1966 | Manyik et al. ........................ | 252/429 |
| 3,300,458 | 1/1967 | Manyik et al. ........................ | 260/88.2 |
| 4,544,762 | 10/1988 | Kaminsky et al. .................... | 556/179 |
| 4,665,208 | 5/1987 | Welborn, Jr. et al. .............. | 556/179 |
| 4,730,071 | 3/1988 | Schoenthal et al. ................ | 556/179 |
| 4,730,072 | 3/1988 | Schoenthal et al. ................ | 556/179 |
| 4,772,736 | 9/1988 | Edwards et al. ..................... | 556/179 |

Primary Examiner—Arthur C. Prescott
Attorney, Agent, or Firm—Joseph D. Odenweller

[57] ABSTRACT

Hydrocarbylaluminoxanes are made by introducing liquid water into the free space above an inert hydrocarbon solution of a hydrocarbyl aluminum compound (e.g. trimethyl aluminum) with intensive agitation while maintaining the reaction temperature at −80° C. up to −10° C.

18 Claims, No Drawings

ALKYLALUMINOXANE PROCESS

BACKGROUND OF THE INVENTION

Complexes of hydrocarbylaluminoxanes with transition metal compounds have been found to be very effective olefin polymerization catalysts (Manyik et al. U.S. Pat. No. 3,242,099).

Hydrocarbylaluminoxanes can be made by the controlled partial hydrolysis of hydrocarbyl aluminum compounds. A problem encountered in doing this is the extremely high reactivity of the aluminum compounds. For example, trimethyl aluminum and triethyl aluminum react explosively with water. Even minor changes in the process can give a significant difference in the product. Accordingly, research on the preparation of hydrocarbylaluminoxanes has been directed at ways to control the reaction of hydrocarbyl aluminum compound with water so that it forms the desired aluminoxane having high activity when used as a co-catalyst and not insoluble gels or, worse yet, explosions.

A further problem is the difficulty in controlling the degree of polymerization of the hydrocarbyl aluminum. Aluminoxanes can exist in the form of linear or cyclic polymers. Each form and chain length can give different catalytic activity. The most difficult aluminoxane preparation to control is the synthesis of methylaluminoxane. Preparations carried out in apparently the same manner frequently lead to different products.

The simplest methylaluminoxane is tetramethylaluminoxane, $(CH_3)_2AlOAl(CH_3)_2$. This can disproportionate to trimethyl aluminum and higher aluminoxane polymers. For this reason, long term storage of methylaluminoxane should be avoided.

Manyik et al., U.S. Pat. No. 3,242,099, report the preparation of alkylaluminoxane by adding water to an inert hydrocarbon solution of alkylaluminum at 0–100° C., preferably 10–65°) C.

Manyik et al. U.S. Pat. No. 3,300,458 disclose a continuous process for making hydrocarbylaluminoxanes by mixing a solution of a hydrocarbyl aluminum compound with a wet solvent at 5° C. up to the boiling point of the solvent.

Kaminsky et al. U.S. Pat. No. 4,542,199 describe the preparation of methylaluminoxane by suspending $CuSO_4.5H_2O$ in toluene and adding trimethyl aluminum to the suspension. The water of crystallization is less readily accessible and serves to moderate the reaction.

Kaminsky et al. U.S. Pat. No. 4,544,762 report a similar process using hydrated aluminum salts as the water source. Welborn, Jr., et al. U.S. Pat. No. 4,665,208 describe the same procedure but with other metal salt hydrates.

More recently, Schoenthal et al. U.S. Pat. No. 4,730,071 describe a process in which a solution of trialkyl aluminum in an inert solvent is added to an ultrasonically induced dispersion of water in an inert solvent to form an alkylaluminoxane. Schoenthal et al. U.S. Pat. No. 4,730,072 is similar except the water dispersion is formed using a high shear impeller.

Edwards et al. U.S. Pat. No. 4,772,736 disclose a process in which water is introduced below the surface of a solution of a hydrocarbyl aluminum compound at a location such that the water is immediately dispersed into the solution which is maintained at a temperature of 5–70° C.

SUMMARY

It has now been discovered that hydrocarbylaluminoxanes can be prepared in high yield and excellent catalytic activity by merely feeding water into the vapor space above a solution of a hydrocarbyl aluminum compound while maintaining the reaction mixture at −10° down to −80° C., more preferably at −50° to −80° C.

DESCRIPTION OF THE PREFERRED EMBODIMENTS

A preferred embodiment of the invention is a process for making aluminoxanes, said process comprising:
(A) placing an inert hydrocarbon solution of a hydrocarbyl aluminum compound in a reaction vessel under an inert atmosphere, said inert hydrocarbon having a freezing point below the reaction temperature,
(B) maintaining said solution at a reaction temperature in the range of about −80° up to −10° C. and
(C) introducing liquid water into the free-space above the surface of said solution while intensively mixing said solution.

The process is applicable to a broad range of hydrocarbyl aluminum compounds such as aluminum trialkyls, aluminum triaryls, mixed alkyl aryl aluminum, alkyl aluminum dihalide, dialkyl aluminum halide, alkyl aluminum sesquihalides, diaryl aluminum halides and the like.

A few representative examples are trimethyl aluminum, triethyl aluminum, triisobutyl aluminum, trihexylaluminum, trioctyl aluminum, triphenyl aluminum, dimethyl phenyl aluminum, tricyclohexyl aluminum, dimethyl aluminum chloride, diethyl aluminum chloride, ethyl aluminum dibromide, diisobutyl aluminum chloride, methyl aluminum sesquichloride, ethyl aluminum sesquichloride, propyl aluminum sesquibromide and the like.

The catalysts most in demand are made from trialkyl aluminums, especially the tri lower-alkyl aluminums such as those in which the alkyl group contains 1-carbon atoms such as trimethyl aluminum, triethyl aluminum and triisobutyl aluminum. The most preferred aluminum compound is trimethyl aluminum. Unfortunately this is the most reactive of the aluminum alkyls. Its reaction with water is most difficult to control compared to higher aluminum alkyls such as triisobutyl aluminum.

The inert hydrocarbon solvents include any aliphatic or aromatic compound that will remain liquid at the low reaction temperatures and form at least a 5 weight percent solution of the hydrocarbyl aluminum. The critical low reaction temperatures used in the process range from −10° C. down to −80° C. or lower. Hence the solvent must have a freezing point below −10° C. and preferably much lower. Some examples of such solvents and their freezing points are toluene (−95° C.), ethylbenzene (−95° C.), n-propyl benzene (−99.5° C.), isopropyl benzene (−96° C.), n-butyl benzene (−88° C.), m-xylene (−48° C.), n-hexane (−95° C.) and isohexane (−153° C.). The most preferred solvent is toluene.

The amount of hydrocarbyl aluminum dissolved in the inert solvent should be kept low. A useful range in which to operate is about 1–20 weight percent hydrocarbyl aluminum in the solution. A preferred range is about 5–10 weight percent.

The hydrocarbyl aluminum solution is placed in the reaction vessel under an inert gas (e.g. nitrogen, argon) atmosphere. The reaction vessel is fitted with an agitator system capable of intensive mixing. The preferred agitator is a high-shear turbine-type impeller. This is the type impeller frequently used to prepare sodium dispersions.

Water used in the reaction should be fairly pure to avoid contamination of the hydrocarbylaluminoxane which might affect its utility in preparing polymerization catalyst. Distilled deionized water is preferred.

The water is introduced into the free space of the reaction vessel above the liquid surface. The water is liquid water and not water vapor or merely wet solvent or water dispersed in an inert solvent. The water preferably drops into the hydrocarbyl aluminum solution at a location above the intensive agitator.

The process can be conducted in a batch or continuous mode. In the batch process all of the hydrocarbyl aluminum solution is placed in the reactor and all of the water is added either all at once, in increments or continuously.

In the continuous process both hydrocarbyl aluminum solution and water are continuously fed to a reactor under process conditions. Concurrently reaction mixture is withdrawn to maintain a constant liquid volume. The rate of feed and withdrawal is adjusted to give an average residence time of about 5 minutes to 2 hours or more. The withdrawn liquid can be filtered and used as is to prepare polymerization catalyst or it can be concentrated by evaporating solvent.

In another mode of continuous operation the reaction of water with the hydrocarbyl aluminum is only partially complete (e.g. 50–90 percent complete) in the first reactor and the withdrawal stream is transferred to a second stirred reactor where the reaction is completed. In this mode of operation the temperature in the second reactor can be somewhat higher because most of the reactants have already reacted. A useful temperature range in the second or subsequent reactor is about $-80°$ C. up to about 25° C.

In a further modification of the continuous process only part of the water is fed to the free space of the first reactor (e.g. 20–80 percent of the total water). The remaining water is fed to the second and/or subsequent reactors. The result is a multi-stage continuous reactor with water feed to two or more reactors. In this mode the temperature is maintained at $-10°$ C. down to $-80°$ C., preferably $-50°$ C. to $-80°$ C., in each reactor to which water is added.

The amount of water can vary depending on the desired product. The stoichiometric amount of water for tetramethylaluminoxane, $(CH_3)_2AlOAl(CH_3)_2$, is 0.5 moles per mole of trimethylaluminum. The stoichiometric amount of water for a linear or cyclic polymer is 1 mole per mole of trimethyl aluminum. In practice the amount of water used is between these extremes, preferably about 0.6–0.9 moles and more preferably 0.7–0.8 moles per mole of hydrocarbyl aluminum compound.

The water displaces the hydrocarbyl group forming hydrocarbon. When these groups are lower alkyls such as methyl or ethyl, they will evolve as methane or ethane. Higher displaced groups (e.g. propane, butane) might not evolve until the reaction is complete and raised to room temperature. Still higher hydrocarbyl groups will form by-products that can remain in the product as solvent, e.g. hexane, octane, benzene and the like).

In making methylaluminoxane ("MAO") the progress of the reaction can be followed by measuring the evolved methane. Each mole of water that reacts should form 2 moles of methane (44.8 L at STP). Evolved gas volumes below this indicate less than 100 percent completion.

Another criteria used to monitor the product uniformity is the evolved gas/aluminum ratio. For tetramethylaluminoxane the evolved gas/aluminum ratio is 1.0 mole gas per mole of trimethyl aluminum. For cyclic or long chain linear polymer the evolved gas/aluminum ratio is 2.0. The actual ratio gives an indication of the product distribution.

It is critical that the process is conducted at very low temperatures below the freezing point of the added water. A useful temperature range is $-10°$ C. down to $-80°$ C. or lower if the inert solvent does not freeze. A preferred reaction temperature is below $-20°$ C., more preferably below $-30°$ C. and most preferably below $-40°$ C.

The following examples show how the reaction can be conducted.

EXAMPLE 1

In a glass reaction flask fitted with a gas outlet tube to a wet test gas volume meter, a thermocouple well, a septum cap and a high speed turbine type impeller driven by an industrial die grinder motor (no load rating 25,000 RPM) was placed a solution of 14.3 g (0.198 mole) of trimethyl aluminum in 162.2 g dry toluene. The solution was maintained under a nitrogen atmosphere. The solution was cooled to $-68°$ C. and the stirrer turned to near maximum output. Using a syringe, 2.14 g (0.119 mole) of distilled deionized water was injected through the serum cap into the free space above the liquid over a 10 minute period. The following table shows the reaction temperature profile and evolved gas.

| Reaction Time (Min) | Temperature (°C.) | Evolved Gas (L) |
| --- | --- | --- |
| 0 | $-68$ | — |
| 10 | $-61$ | 0.6 |
| 15 | $-55$ | 1.55 |
| 20 | $-60$ | 1.90 |
| 25 | $-63$ | 2.1 |
| 50 | $-50$ | 4.0 |
| 60 | $-53$ | 4.5 |
| 70 | $-52$ | 4.8 |
| 80 | $-48$ | 5.1 |
| 95 | $-38$ | 5.3 |
| 120 | $+24$ | 6.2 |

The total gas evolution was first corrected ($-0.5$ L) for warming the initial flask free space (800 ml) from $-68°$ C. to $+24°$ C. to give 5.7 L at 24° C. which was converted to standard temperature-pressure (STP) to net 5.22 L at STP. Theory for 0.119 mole water reaction ($0.119\times2\times22.4$) is 5.33 L so actual gas evolution was 97.9 percent of theory. The gas/aluminum ratio calculated to 1.78. The product was initially a water-clear solution but developed some haze and a small amount of gel on standing.

EXAMPLE 2

This experiment was conducted in the same equipment used in Example 1. The flask was charged with 163.3 g toluene and 16.1 g (0.223 mole) trimethyl aluminum. The flask was cooled to $-69$ and 2.41 g (0.134 mole) water injected incrementally into the free space over a 3 hour 15 minute period.

| Reaction Time (Min) | Temperature (°C.) | Evolved Gas (L) |
| --- | --- | --- |
| 0 | −69 | — |
| 30 | −61 | 0.7 |
| 60 | −61 | 1.1 |
| 90 | −60 | 1.4 |
| 105 | −60 | 1.65 |
| 120 | −60 | 2.45 |
| 150 | −58 | 3.3 |
| 170 | −58 | 4.0 |
| 195 | −57 | 4.9 |
| (all water in) | | |
| 225 | −58 | 5.85 |
| 240 | −56 | 6.1 |
| (cooling stopped) | | |
| 260 | −39 | 6.6 |
| 270 | −38 | 6.7 |
| 285 | +24 | 7.3 |

Correcting for warm-up and converting to STP gives 6.4 L (107 percent of theory). The gas/aluminum ratio was 1.72 (theory is 1.8).

EXAMPLES 3-6

These examples were all conducted by placing 19 ml (0.197 moles) of trimethyl aluminum/toluene solution (8.05 weight percent TMA) in a round bottom flask fitted with a high speed stirrer. The solution was cooled and 2.12 g of water was fed dropwise above the liquid phase at the temperature shown in the following table.

| | Water Feed | Reaction |
| --- | --- | --- |
| Example | Time (min) | Temp (°C.) |
| 3 | 30 | 10°[1] |
| 4 | 20 | 5° |
| 5 | 15 | −10°[2] |
| 6 | 20 | −30°[3] |

Stirring was continued after completion of water feed for about 30 minutes at ambient temperature.

The main use of alkylaluminoxanes is as a co-catalyst with a transitional metal compound in the polymerization of olefins to make syndiotactic polymers. Chemical analysis of various alkylaluminoxanes can be very similar even when the catalytic activity of the products differ greatly. For this reason the products are preferably evaluated using a polymerization test. One such test involves the polymerization of ethylene under pressure in dry toluene containing MAO and a zirconium compound. The amount of MAO, zirconium compound and ethylene is the same in each test. After the polymerization is complete, the polyethylene is recovered, dried and weighed. The test criteria is the amount of polyethylene formed. The following table gives the results for the 10° C. and −30° C. examples.

| MAO Reaction Temperature | Polyethylene Yield |
| --- | --- |
| 10° C. | 4.0 g |
| −30° C. | 15.1 g |

These results show the importance of low temperature in the MAO process.

I claim:

1. A process for making aluminoxanes, said process comprising:
    (A) placing an inert hydrocarbon solution of a hydrocarbyl aluminum compound in a reaction vessel under an inert atmosphere, said inert hydrocarbon having a freezing point below the reaction temperature,
    (B) maintaining said solution at a reaction temperature in the range of about −80° up to −10° C. and
    (C) introducing liquid water into the free-space above the surface of said solution while intensively mixing said solution.
2. A process of claim 1 wherein said hydrocarbyl aluminum compound is a trialkyl aluminum.
3. A process of claim 2 wherein said trialkyl aluminum is triisobutyl aluminum.
4. A process of claim 2 wherein said trialkyl aluminum is trimethyl aluminum.
5. A process of claim 1 wherein said inert hydrocarbon is an inert aromatic hydrocarbon.
6. A process of claim 5 conducted at a temperature below −20° C.
7. A process of claim 5 conducted at a temperature below −30° C.
8. A process of claim 5 conducted at a temperature below −40° C.
9. A process of claim 5 wherein said aromatic hydrocarbon is selected from toluene, ethylbenzene, isopropylbenzene, n-propylbenzene, n-butylbenzene, sec-butylbenzene, isobutylbenzene or tert-butylbenzene or mixtures thereof.
10. A process of claim 9 wherein said aluminum compound is a trialkyl aluminum compound.
11. A process of claim 10 wherein said trialkyl aluminum is triisobutyl aluminum.
12. A process of claim 11 conducted at a temperature below −20° C.
13. A process of claim 12 wherein said inert hydrocarbon is toluene.
14. A process of claim 10 wherein said trialkyl aluminum is trimethyl aluminum.
15. A process of claim 14 conducted at a temperature below −20° C.
16. A process of claim 15 wherein said inert hydrocarbon is isopropylbenzene.
17. A process of claim 15 wherein said inert hydrocarbon is toluene.
18. A process of claim 17 wherein the amount of water is about 0.5-1.0 moles per mole trimethyl aluminum.

* * * * *